United States Patent
Najafi et al.

(10) Patent No.: US 8,014,865 B2
(45) Date of Patent: Sep. 6, 2011

(54) METHOD FOR MONITORING A PHYSIOLOGIC PARAMETER OF PATIENTS WITH CONGESTIVE HEART FAILURE

(75) Inventors: Nader Najafi, Ann Arbor, MI (US); Collin A. Rich, Ypsilanti, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 791 days.

(21) Appl. No.: 11/459,065

(22) Filed: Jul. 21, 2006

(65) Prior Publication Data

US 2007/0032734 A1 Feb. 8, 2007

Related U.S. Application Data

(62) Division of application No. 10/677,694, filed on Oct. 2, 2003, now Pat. No. 7,615,010.

(60) Provisional application No. 60/415,537, filed on Oct. 3, 2002, provisional application No. 60/415,538, filed on Oct. 3, 2002, provisional application No. 60/416,406, filed on Oct. 7, 2002, provisional application No. 60/416,407, filed on Oct. 7, 2002, provisional application No. 60/416,408, filed on Oct. 7, 2002, provisional application No. 60/416,409, filed on Oct. 7, 2002.

(51) Int. Cl.
*A61B 5/0215* (2006.01)

(52) U.S. Cl. ............................ 607/23; 600/486; 600/488
(58) Field of Classification Search .................. 607/23; 600/486, 488
See application file for complete search history.

(56) References Cited

U.S. PATENT DOCUMENTS

| | | | | |
|---|---|---|---|---|
| 6,328,699 | B1 * | 12/2001 | Eigler et al. ................. | 600/486 |
| 6,409,674 | B1 * | 6/2002 | Brockway et al. ............ | 600/486 |
| 6,783,499 | B2 * | 8/2004 | Schwartz ...................... | 600/486 |
| 7,058,450 | B2 * | 6/2006 | Struble et al. ................. | 607/18 |
| 2002/0120200 | A1 * | 8/2002 | Brockway et al. ............ | 600/488 |

* cited by examiner

*Primary Examiner* — Michael Kahelin
(74) *Attorney, Agent, or Firm* — Hartman & Hartman, P.C.; Gary M. Hartman; Domenica N. S. Hartman

(57) ABSTRACT

A method of monitoring physiological parameters for diagnosis and treatment of congestive heart failure in a patient. The method includes implanting at least one sensing device in a cavity of the patient's cardiovascular system, preferably so that the sensing device passes through and is anchored to a septum of the heart and, to minimize the risk of thrombogenicity, a larger portion of the sensing device is located in the right side of the heart and a smaller portion of the sensing device is located in the left side of the heart. Electromagnetic telecommunication and/or wireless powering of the sensing device is performed with an external readout device. The method can be used to perform effective monitoring, management, and tailoring of treatments for patients suffering from congestive heart failure, as well as many other diseases.

28 Claims, 3 Drawing Sheets

METHOD FOR MONITORING A PHYSIOLOGIC PARAMETER OF PATIENTS WITH CONGESTIVE HEART FAILURE

CROSS REFERENCE TO RELATED APPLICATIONS

This is a division patent application of U.S. patent application Ser. No. 10/677,694, filed Oct. 2, 2003, (now U.S. Pat. No. 7,615,010) which claims the benefit of U.S. Provisional Application Nos. 60/415,537 filed Oct. 3, 2002, 60/415,538 filed Oct. 3, 2002, 60/416,406 filed Oct. 7, 2002, 60/416,407 filed Oct. 7, 2002, 60/416,408 filed Oct. 7, 2002, and 60/416,409 filed Oct. 7, 2002. The contents of these prior applications are incorporated herein by reference.

BACKGROUND OF THE INVENTION

The present invention relates generally to the field of implantable medical devices for monitoring physiological parameters. More particularly, the invention relates to a method and system utilizing a telemetric implantable physiologic sensor for monitoring patients with Congestive Heart Failure and tailoring their medical management.

Congestive heart failure (CHF) is a condition in which a damaged or overworked heart cannot pump adequately to meet the metabolic demands of the body and/or can do so only with an elevated ventricular diastolic pressure. CHF is a major health problem worldwide, affecting millions of patients and accounts for numerous hospitalizations. Overall, the cost of treating CHF is very high (billions of dollars annually) and involves numerous physician visits. From 1979 to 1999, CHF deaths increased 145% and hospital discharges increased 155%. Survival is poor with 20% dying within one year and only 50% of patients surviving more than 5 years. The many patients suffering from this progressive, fatal disease tend to have an extremely poor quality of life and become increasingly unable to perform routine daily tasks.

Left ventricular (LV) filling pressure is a key factor in the progression of CHF. LV filling pressure represents the diastolic pressure at which the left atrium (LA) and left ventricle (LV) equilibrate, at which time the LV fills with blood from the LA. As the heart ages, cardiac tissue becomes less compliant, causing the LV filling pressure to increase. This means that higher pressures are required from the LA in order to fill the LV. The heart must compensate for this in order to maintain adequate cardiac output (CO); however, increasing the LA pressure strains the heart and over time irreversible alteration will occur.

Left Ventricular End Diastolic Pressure (LVEDP) and Mean Left Atrium Pressure (MLAP) (see FIG. 1) are the primary factors physicians use to evaluate CHF patients. MLAP and LVEDP correspond directly with LV filling pressure and are easy for physicians to identify from LV pressure data. The physician's ultimate goal is to increase cardiac output (CO) while reducing LVDEP. Treatment methods include medications, lifestyle changes, pacemakers, and/or surgery.

The only current method for evaluating intracardiac pressures, including MLAP and LVEDP, is invasive, namely, a cardiac catheterization procedure. Catheterization, however, provides only a snapshot of pressure data, carries morbidity, and is expensive. Following diagnosis of congestive heart failure, physicians would prefer to noninvasively monitor heart condition on a continuing basis in order to optimize treatment. Currently, no technology exists that has this capability.

Furthermore, in certain cases, CHF is complicated by mitral stenosis. This is a very complex situation and requires significantly more precise and continuous pressure data. Atrial fibrillation can develop as a result of this condition, and catheterization to evaluate such cases is considerably more complex since pressure gradients across the mitral valve must also be measured. Doppler echocardiography can be used to evaluate this condition; however, echocardiography again requires a specialized laboratory with specialized equipment and doesn't provide continuous measurements.

The treatment of cardiovascular diseases such as Chronic Heart Failure (CHF) can be greatly improved through continuous and/or intermittent monitoring of various pressures and/or flows in the heart and associated vasculature. Porat (U.S. Pat. No. 6,277,078), Eigler (U.S. Pat. No. 6,328,699), and Carney (U.S. Pat. No. 5,368,040) each teaches different modes of monitoring heart performance using wireless implantable sensors. In every case, however, what is described is a general scheme of monitoring the heart. The existence of a method to construct a sensor with sufficient size, long-term fidelity, stability, telemetry range, and biocompatibility is noticeably absent in each case, being instead simply assumed. Eigler, et al., come closest to describing a specific device structure although they disregard the baseline and sensitivity drift issues that must be addressed in a long-term implant. Applications for wireless sensors located in a stent (e.g., U.S. Pat. No. 6,053,873 by Govari) have also been taught, although little acknowledgment is made of the difficulty in fabricating a pressure sensor with telemetry means sufficiently small to incorporate into a stent.

BRIEF SUMMARY OF THE INVENTION

The invention comprises a telemetric sensing system and method for monitoring physiologic parameters used to evaluate heart condition in CHF patients. The system includes an implantable sensor unit and a companion reader unit. The sensor unit comprises an anchoring mechanism, at least one inductor coil, and at least one sensor operating to sense at least one physiological parameter. The sensing unit is implanted so that a portion of the anchoring mechanism passes through a septum of the heart and, to minimize the risk of thrombogenicity, a larger portion of the sensing device is located in the right side of the heart and a smaller portion of the sensing device is located in the left side of the heart and includes the at least one sensor. The sensor unit is preferably batteryless and wireless, and may be delivered percutaneously (for example, by catheter) or surgically. Once in place, the sensor unit is wirelessly interrogated with the reader unit.

Upon implanted in the heart, the sensor unit is capable of measuring and transmitting, in real time, any of various physiologic parameters including Left Ventricular End Diastolic Pressure (LVEDP), Left Atrium Pressure, and Mean Left Atrium Pressure (MLAP). When desired, the sensor unit is also able to monitor other parameters, including but not limited to blood flow and blood chemistry. Monitoring one or more of these parameters gives the physician several advantages: Enables earlier diagnosis of a failing heart; Facilitates earlier intervention in the course of a disease; Enables better tailoring of medications or other treatments and therapies to maximize cardiac output while reducing LVEDP; Facilitates the identification of other complications from treatments or disease progression (e.g. weakening of other heart chambers); Gives faster feedback on the impact of medications and/or pacing changes on heart function; Facilitates defibrillator or pacemaker optimization; Lowers overall treatment costs; Decreases frequency and/or severity of hospitalization for CHF-related conditions through improved outpatient and home care monitoring; Can be incorporated into an early warning system for serious conditions; Enables closed-loop medical delivery systems.

DETAILED DESCRIPTION OF THE INVENTION

The following description of preferred embodiments and methods provides examples of the present invention. The embodiments discussed herein are merely exemplary in nature, and are not intended to limit the scope of the invention in any manner. Rather, the description of these preferred embodiments and methods serves to enable a person of ordinary skill in the relevant art to make, use and perform the present invention.

In order to provide for the effective monitoring, management, and tailoring of treatments for congestive heart failure, the present invention provides a wireless sensing system. The system comprises an implantable monitor in the form of a sensor which is securely anchored in a cavity of the heart; and an external reader that may transmit power to and receive transmitted data from the sensor. Data transmitted from the sensor may include pressure, temperature, calibration data, identification data, fluid flow rate, chemical concentration, and/or other physiologic parameters.

In the preferred embodiment, the sensor transmits data corresponding to Left Ventricular End Diastolic Pressure (LVEDP) or Mean Left Atrium Pressure (MLAP). To accomplish this, the sensor is located such that it reads pressure in the left ventricle (LV) or Left Atrium (LA). Alternatively, pressures correlated to LVEDP or MLAP may be transmitted if the sensor is located such that it reads pressures from the wedge position in the pulmonary artery. Furthermore, additional useful pressure data for monitoring CHF or other cardiovascular diseases may be obtained (by suitable location of the sensor) from pressures in the LA, aorta, right ventricle (RV), right atrium (RA), or pulmonary artery (PA). Note that the sensor may be located directly in the cavity whose pressure is being monitored, or it may be located in an intermediary structure, such as the atrial or ventricular septum, as long as communication with the parameter of interest is maintained.

In addition to LVEDP and MLAP, data useful to the physician and measurable with the described invention (in conjunction with appropriate mathematical algorithms) include, but are not limited to: dp/dt (pressure change over time) of the LV pressure, dp/dt of the LA pressure, dp/dt of the RV pressure, RVEDP, and mean RA pressure. Each of these may be measured and/or derived from pressures measured in the appropriate heart cavities.

For cases of CHF with mitral valve stenosis, a second sensor would be placed such that mitral valve gradient can be assessed (for example, one sensor in the LA and one in the LV). This allows assessment of the severity of mitral disease using the pressure gradient. Ultimately, this would provide critical information to help the physician decide whether to proceed with early valve surgery and/or balloon angioplasty/valvuloplasty.

Figure 1:
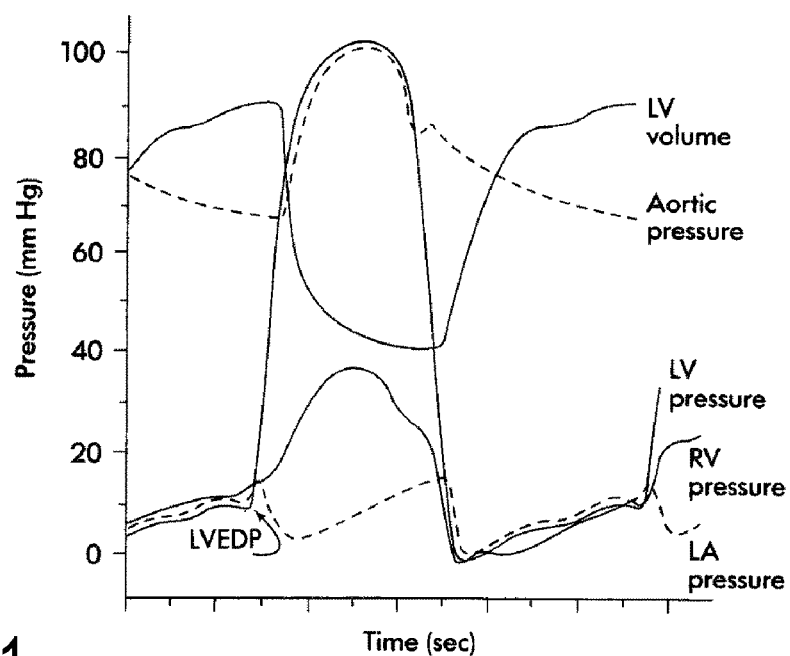
FIG. 1 is a graph of the expected waveforms for various pressure points within the heart.
Figure 2:
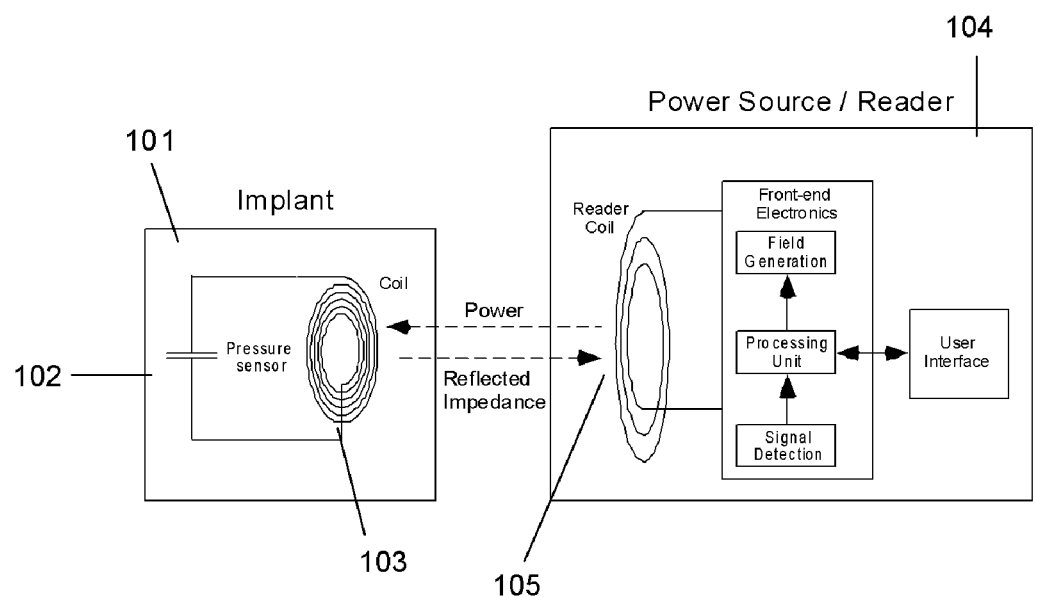
FIG. 2 is a block diagram of a magnetic telemetry based physiologic monitoring system based on a resonant scheme according to a preferred embodiment of the present invention.

The wireless telemetry link between the sensor and the reader is preferably implemented using either a resonant or passive, magnetically coupled scheme. A resonant device 101 (shown in FIG. 2) is the simplest approach, and consists only of a packaged inductor coil 103 and capacitive pressure sensor 102. Together, the sensor 102 and coil 103 form a circuit that has a specific resonant frequency. At that resonant frequency, the circuit presents a measurable change in magnetically coupled impedance load to an external coil 105 associated with an external reader 104. Because the resonant frequency is a function of the inductance of the coil 103 and the capacitance of the sensor 102, as pressure changes the resonant frequency changes as well. The external reader 104 is able to determine pressure by monitoring the frequency at which the coil antenna 105 impedance changes.

Figure 3:
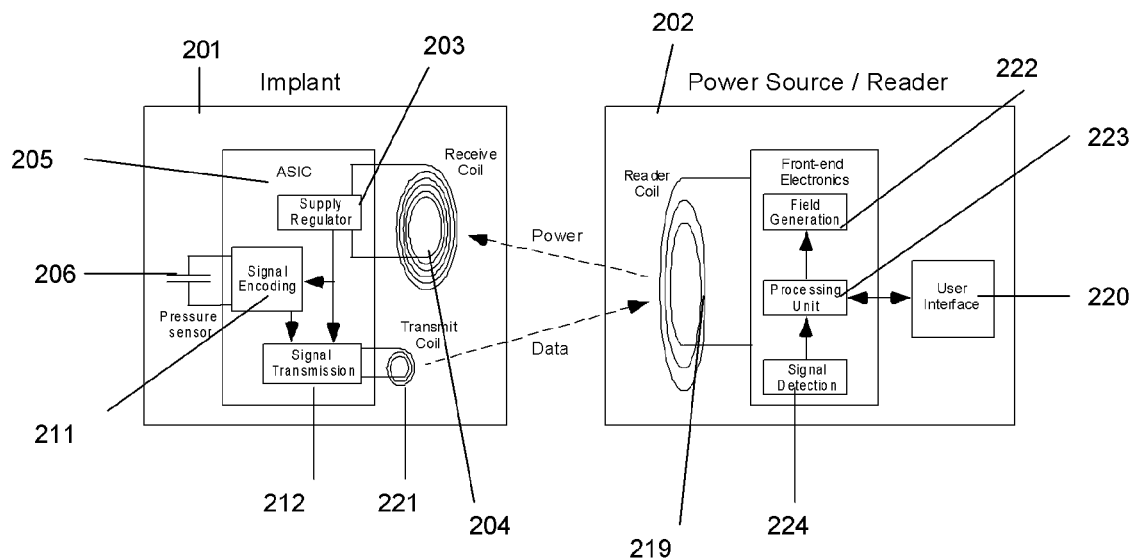
FIG. 3 is a block diagram of a magnetic telemetry based physiologic monitoring system based on a passive scheme according to an alternate embodiment of the present invention.

The preferred communication scheme for the present invention, shown in FIG. 3 as being between a passive implant device 201 and an external reader 202, is based on magnetic telemetry. Devices that have on-board circuitry but still receive their operating power from an external source (i.e., are batteryless) are referred to herein as passive. Without the external reader 202 present, the implant device 201 lays passive and without any internal means to power itself. When a pressure reading is desired, the reader 202 is brought into a suitable range to the implant device 201. In this case the external reader 202 uses an alternating magnetic field to induce a voltage in the implant device 201. When sufficient voltage has been induced in the implant device 201, a rectification circuit 203 converts the alternating voltage on the receiver coil 204 into a direct voltage that can be used by the electronics 205 as a power supply for signal conversion and communication. At this point the implant device 201 can be considered alert and, in the preferred embodiment, also ready for commands from the reader 202. The maximum achievable distance is mostly limited by the magnetic field strength necessary to turn the implant device 201 on. This telemetry scheme has been proven and used extensively in the identification and tracking industry (e.g., implantable RF ID technology from Texas Instruments or Digital Angel) with a great deal of acceptance and success.

Once the direct voltage in the implant device 201 has been established for the circuit operation, a number of techniques may be used to convert the output of the device 201 into a form suitable for transmission back to the reader 202. In the preferred embodiment, a capacitive pressure sensor 206 and sigma delta conversion or capacitance to frequency conversion of the sensor output may be easily used. Capacitive sensors are preferred due to the small power requirements for electronics when reading capacitance values. Many pressure sensors are based on piezoresistive effects and, while suitable for some applications, do suffer in this application due to the higher power levels needed for readout. Sigma delta converters are preferred due to the tolerance of noisy supply voltages and manufacturing variations.

As those skilled in magnetic telemetry are aware, a number of modulation schemes are available for transmitting data via magnetic coupling. The preferred schemes include but are not limited to amplitude modulation, frequency modulation, frequency shift keying, phase shift keying, and also spread spectrum techniques. The preferred modulation scheme may be determined by the specifications of an individual application, and is not intended to be limited under this invention.

In addition to the many available modulation techniques, there are many technologies developed that allow the implant device 201 to communicate back to the reader 202 the signal containing pressure information. It is understood that the reader 202 may transmit either a continuous level of RF power to supply the needed energy for the device 201, or it may pulse the power allowing temporary storage in a battery or capacitor device (not shown) within the device 201. Similarly, the implant device 201 of FIG. 3 may signal back to the reader 202 at any interval in time, delayed or instantaneous, during reader RF (Radio Frequency) transmission or alternately in the absence of reader transmission. The implant device 201 may include a single coil antenna 204 for both reception and transmission, or it may include two antennas 204 and 221, one each for transmission and reception, respectively. There are many techniques for construction of the reader coil 219 and processing electronics known to those skilled in the art. The reader 202 may interface to a display, computer, or other data logging devices 220.

The electronic circuit may consist of the coil antenna 204, rectification circuitry 203, signal conditioning circuitry 211, and signal transmission circuitry 212.

A large number of possible geometries and structures are available for the coil 204 and are known to those skilled in the art. The coil conductor may be wound around a ferrite core to enhance magnetic properties, deposited on a flat rigid or flexible substrate, and formed into a long/skinny or short/wide cylindrical solenoid. The conductor is preferably made at least in part with a metal of high conductivity such as copper, silver, or gold. The coil 204 may alternately be fabricated on implantable sensor substrates. Methods of fabrication of coils on the sensor substrate include but are not limited to one or more or any combination of the following techniques: sputtering, electroplating, lift-off, screen printing, and/or other suitable methods known to those skilled in the art.

The rectification circuitry 203 outputs a constant voltage level for the other electronics from an alternating voltage input. Efficient realizations of such circuitry are standard electronic techniques and may include full bridge diode rectifiers in the preferred embodiment. This rectification circuitry may include a capacitor for transient energy storage to reduce the noise ripple on the output supply voltage. This circuitry may be implemented on the same integrated circuit die with other electronics.

The signal conditioning circuit 211 processes an output signal from the sensor 206 and prepares it for transmission to an external receiving and/or analyzing device. For example, many pressure sensors output a capacitance signal that may be digitized for radio frequency (RF) transmission. Accordingly, the signal conditioning circuit 211 places the output signal of the sensor into an appropriate form. Many different signal conditioning circuits are known to those skilled in the art. Capacitance to frequency conversion, sigma delta or other analog to digital conversion techniques are all possible conditioning circuits that may be used in a preferred embodiment.

The signal transmission circuitry 212 transmits the encoded signal from the signal conditioning circuitry 211 for reception by the external reader 202. Magnetic telemetry is again used for this communication, as the transmission circuitry 212 generates an alternating electromagnetic field that propagates to the reader 202. Either the same coil 204 is used for signal reception and for transmission, or alternately the second coil 221 is dedicated for transmission only.

A third option, particularly useful for (but not limited to) situations in which long-term data acquisition without continuous use of the readout unit is desirable, is to implement the sensor using an active scheme. This approach incorporates an additional capacitor, battery, rechargeable battery, or other power-storage element that allows the implant to function without requiring the immediate presence of the readout unit as a power supply. Data may be stored in the sensor and downloaded intermittently using the readout unit as required.

Figure 4:
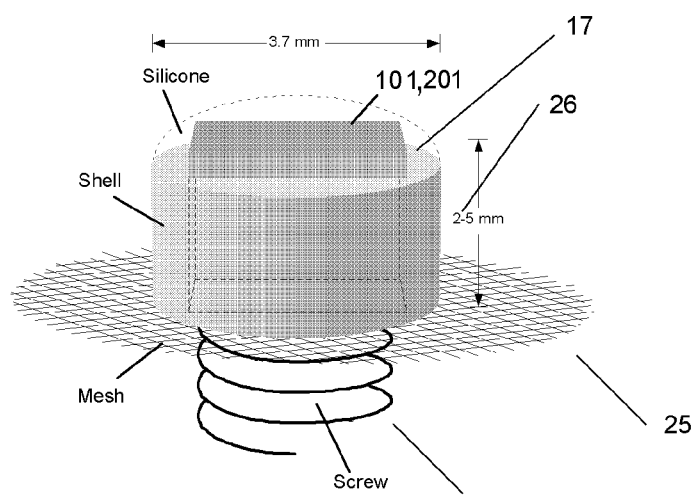
FIG. 4 is a perspective view of a sensor implant incorporating a screw anchoring mechanism according to a preferred embodiment of the present invention.

The implantable sensor may be physically realized with a combination of any of several technologies, including those using microfabrication technology such as Microelectromechanical Systems (MEMS). For example, capacitive and piezoresistive pressure sensors have been fabricated with MEMS technology. A hermetic sensor package may be formed from anodically bonded layers of glass and silicon (doped or undoped). Anchoring provisions may be incorporated directly into such a hermetic package, or they may alternately be added with an additional assembly step (e.g. as shown in FIG. 4). An example of this would be insertion of the package into a molded plastic or metal shell that incorporates anchoring provisions. Possible anchoring methods include those conventionally used for cardiac pacing leads, such as screws or tines, as well as septal occluder schemes. Many such packaging schemes are known to those familiar with the art, and the present description should not be construed as limiting.

In addition to the basic implant-and-reader system, a number of other embodiments of the technology can be realized to achieve additional functionality. The system may be implemented as a remote monitoring configuration, including but not limited to home monitoring, which may include but not limited to telephone based, wireless communication based, or web-based (or other communication means) delivery of information received from the implant by the reader to a physician or caregiver.

Figure 6:
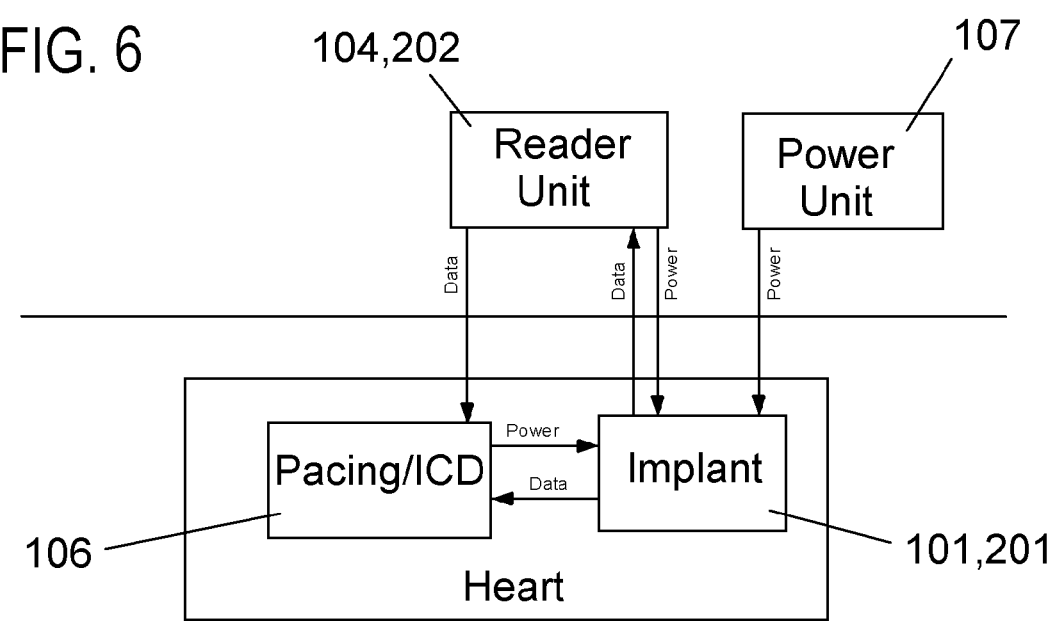
FIG. 6 is a block diagram of a closed-loop pacing/ICD tuning system incorporating the magnetic telemetry-based physiologic monitoring system of the present invention.

The system may be implemented as a closed-loop pacing/ICD (Implantable Cardioverter Defibrillator) tuning system as represented in FIG. 6, in which sensor data is fed to a patient pacemaker of a pacing/ICD unit 106 for tailoring of pacing/ICD function. The implanted sensor device 101/201 may be directly interrogated by the pacing/ICD unit 106 (i.e. without requiring the intermediate external reader 104/202). It may also be interrogated by the pacing/ICD unit 106, but with an additional, external power unit 107 solely for transmitting power to the sensor device 101/201. Alternatively, the sensor data may first be transmitted to an external reader 104/202 and then re-transmitted to the pacing/ICD unit 106. Finally, the system may be configured such that both an external reader 104/202 and the pacing/ICD unit 106 may interrogate and/or power the sensor device 101/201.

A closed-loop drug delivery system may also be envisioned. Data from the implanted sensor is fed directly to a drug delivery device (which may or may not be implanted, and may or may not be an integral part of the implanted sensor). This approach would allow continuous adjustment of medications for CHF-related conditions with minimal physician intervention.

Implanted sensor data may be used as feedback for a LA to RA unidirectional valve, which can be used to prevent pulmonary edema. LA decompression is accomplished by allowing blood to flow directly from the LA to the RA, thus reducing the pressure in the LA and the pulmonary bed.

The implantable sensor can be any suitable miniature sensor adapted to detect and/or monitor various physiological parameters. For example, the sensor can comprise a pressure sensor, a temperature sensor, a flow sensor, a velocity sensor, or a sensor adapted to measure specific chemistries such as gas content (e.g., O2 and CO2) and glucose levels. Various specific examples of these types of miniature sensors are known to those skilled in the art, and any one or more of these suitable sensors can be utilized in the sensor module of the present invention. While the specific type of sensor(s) chosen will depend on the application of the implantable system, the sensor(s) should be of a sufficiently small size in order to facilitate placement within a catheter for delivery and implantation.

To limit the risk of thrombogenesis, the preferred embodiment has limited protrusion of volume into the blood stream (particularly in the left side of the heart), as both shape and size are factors in thrombogenesis. Another shell may be overmolded or preformed to house the glass/silicon module, and the outer shell contains the necessary apparatus for anchoring the implant. In a preferred embodiment, the outer shell may be formed with existing plastic injection technologies suitable for medical implantation. A coating, preferably of silicone, parylene and/or polymers provides a non-thrombogenic exterior for the biologic environment.

The implant may be located in various places depending on the blood pressure measurement of interest. For chronic heart failure the end-diastolic pressure or mean left atrium pressure may be of most importance, and therefore the left chambers of the heart or immediately attaching vessels may be preferred locations. Because the number of implants is not practically limited by the technology, multiple locations for blood pressure and/or other physiologic parameter measurements are easily established, including all chambers of the heart, major arteries and appendages. The atrial septum is the preferred embodiment, represented in FIG. 5, since embedding the module in the atrial septum does not significantly impede blood flow and thus minimizes the thrombogenic effect of flow turbulence caused by this volume.

Figure 5:
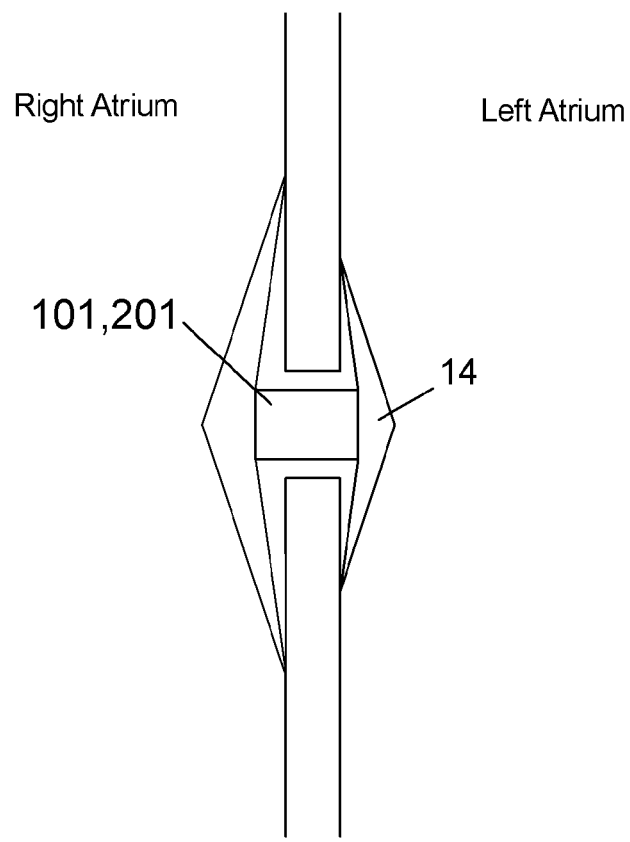
FIG. 5 is a side view of a sensor implanted in the atrial septum according to a preferred embodiment of the present invention.

The implant may be modified with anchoring methods found on devices already used for implantation. Devices such as septal occluders, pacemaker leads, left atrial appendage occluders, etc., may be used as carriers for the current invention. Devices have been made and approved by the FDA to occlude atrial septum defects (a septal occluder) and other vascular holes. An umbrella structure 14 comprising, for example, oppositely-disposed foldable umbrella structures having vertices that face away from each other as shown in FIG. 5, may be folded inside a catheter for delivery and then expanded for implantation. In a preferred embodiment, the present invention may be anchored to the septum with similar techniques, as shown in FIG. 5. An important aspect of this preferred embodiment is that the majority of the implantable sensing device is located in the right side of the heart, with minimum protrusion in the left side of the heart. This embodiment will greatly reduce the thrombogenicity.

Pacemaker leads have a well-established history for implantation methods, and similar techniques are possible for the current invention. A screw 13 (FIG. 4) or barb may be used to attach the implant to a heart or vessel wall. In the first package option shown in FIG. 4, a screw 13 may be molded into the device shell 26, and screwed into the ventricle wall so that the screw buries below the wall surface. In addition, the package may have mesh 25 attached to the device to promote tissue growth and anchoring.

A second package option can be attached with a metal tine or barb placed with a catheter. These devices work well in trabeculated areas of the heart, and therefore are used often for implanting pacing leads in the right ventricle. Clips or expanding probes may also be used, both of which would penetrate the heart or vessel wall slightly.

Note that in addition to sensing physiologic parameters, the described system could be augmented with various actuation functions. In such case, the implant device would be augmented with any of various actuators, including but not limited to: thermal generators; voltage or current sources, probes, or electrodes; drug delivery pumps, valves, or meters; microtools for localized surgical procedures; radiation-emitting sources; defibrillators; muscle stimulators; pacing stimulators.

The foregoing disclosure includes the best mode devised by the inventors for practicing the invention. It is apparent, however, that several variations in the apparatuses and methods of the present invention may be conceivable by one skilled in the art. Inasmuch as the foregoing disclosure is intended to enable one skilled in the pertinent art to practice the instant invention, it should not be construed to be limited thereby, but should be construed to include such aforementioned variations.

The invention claimed is:

1. A method of monitoring one or more physiological parameters useful in diagnosing and/or treating a cardiovascular disease within a patient, the method comprising:
   providing a sensor comprising a hermetic sensor package containing at least one inductor coil and at least one sensing element operable to sense at least one physiological parameter of the patient, the sensor package having oppositely-disposed first and second portions;
   assembling the sensor with an anchoring mechanism to form an implantable sensing device, the anchoring mechanism comprising oppositely-disposed first and second foldable umbrella structures located adjacent the first and second portions, respectively, of the sensor package, the first and second foldable umbrella structures having vertices that face away from each other, the sensor being assembled with the anchoring mechanism so that the sensor package thereof is between the first and second foldable umbrella structures, the second foldable umbrella structure being smaller than the first foldable umbrella structure;
   implanting the sensing device by folding the first and second foldable umbrella structures of the anchoring mechanism, passing the first or second foldable umbrella structure through a septum of the heart of the patient to locate the second foldable umbrella structure within a cavity on the left side of the patient's heart, and expanding the first and second foldable umbrella structures to engage opposite sides of the septum, wherein the entire sensing device is within the heart, the sensor package is located in the septum and the at least one sensing element senses the at least one physiological parameter in the cavity, wherein the first foldable umbrella structure and the majority of the sensing device are located in the right side of the heart to minimize the risk of thrombogenicity;
   operating the sensor to produce an output based on the at least one physiological parameter within the cavity of the patient;
   coupling the sensor to a non-implantable readout device that is not implanted in the patient, the readout device comprising at least one inductor coil having telemetric means that receives the output of the sensor through the at least one inductor coil of the sensing device; and tailoring a medication treatment for treating the cardiovascular disease of the patient based on the output of the sensor.

2. The method according to claim 1, wherein the at least one sensing element of the sensor comprises at least one capacitive sensing element that capacitively senses the at least one physiological parameter within the cavity.

3. The method according to claim 1, wherein the sensor package contains a battery, and the method comprises wirelessly recharging the battery.

4. The method according to claim 1, wherein the at least one physiological parameter is pressure sensed by the sensor.

5. The method according to claim 4, wherein the pressure is chosen from the group consisting of left ventricular end diastolic pressure, left atrium pressure, left atrium appendage pressure, mean left atrium pressure, pressure within the left side of the heart, pressure within the right side of the heart, right atrium pressure, mean right atrium pressure, right ventricular end diastolic pressure, and differential pressure between the left and right atrium.

6. The method according to claim 4, further comprising the step of calculating changes in the pressure over time (dp/dt).

7. The method according to claim 1, wherein the sensing device sends data directly to a drug delivery device to tailor drug treatment of the patient.

8. The method according to claim 1, wherein a resonant scheme is used to couple the sensing device to the readout device.

9. The method according to claim 1, wherein a passive scheme is used to couple the sensing device to the readout device.

10. The method according to claim 1, wherein an active scheme is used to couple the sensing device to the readout device.

11. The method according to claim 1, wherein the at least one physiological parameter sensed by the sensor is chosen from the group consisting of pressure, temperature, flow, blood composition, blood gas content, chemical composition, acceleration, and vibration.

12. The method according to claim 1, wherein the sensing device is implanted in the atrial septum.

13. The method according to claim 1, wherein the sensing device is implanted in the ventricular septum.

14. The method according to claim 1, wherein the method is part of at least one of the following procedures: early diagnosis of a heart failing due to congestive heart failure related conditions; early intervention in treatment of congestive heart failure related conditions; disease management; identification of complications from congestive heart failure related conditions; identification of complications from cardiovascular disease related conditions; treatment of complications from congestive heart failure related conditions; treatment of complications from cardiovascular disease related conditions; feedback regarding the impact of medication on the heart; pacing adjustments; reduction in frequency and severity of hospitalizations due to cardiovascular diseases; reduction in frequency and severity of hospitalizations due to congestive heart failure; tuning of defibrillator or pacemaker parameters to improve congestive heart failure related conditions; identification of mitral valve stenosis; and treatment of mitral valve stenosis.

15. The method according to claim 1, wherein the readout device is used to perform at least one of the following: remote monitoring of congestive heart failure patients; monitoring of congestive heart failure patients with telephone-based data and information delivery; monitoring of congestive heart failure patients with wireless telephone-based data and information delivery; monitoring of congestive heart failure patients with web-based data and information delivery; closed-loop drug delivery to treat congestive heart failure; closed-loop pacemaker parameter tuning to treat congestive heart failure or congestive heart failure related conditions; warning systems for critical worsening of congestive heart failure or congestive heart failure related conditions; portable or ambulatory monitoring or diagnosis; battery-operation capability; data storage; reporting global positioning coordinates for emergency applications; communication with other medical devices chosen from the group consisting of pacemakers, defibrillators, cardioverter defibrillators, drug delivery systems, non-drug delivery systems, and wireless medical management systems.

16. The method according to claim 1, wherein the sensing device and the readout device are incorporated into a closed-loop system with a left atrium to right atrium unidirectional valve for preventing the development of pulmonary edema.

17. The method according to claim 1, wherein the at least one sensing element of the sensor comprises a barometric pressure sensing element.

18. The method according to claim 17, wherein the barometric pressure sensing element operates to compensate for variations in atmospheric pressure.

19. The method according to claim 1, wherein the sensing device is implanted using a minimally invasive outpatient technique.

20. The method according to claim 1, wherein the sensing device is implanted using a catheter delivery method by folding the first and second foldable umbrella structures within a catheter, and then delivering the sensing device to the septum with the catheter.

21. The method according to claim 1, wherein the first and second foldable umbrella structures of the anchoring mechanism clamp the sensing device to the septal wall.

22. The method according to claim 1, wherein the second foldable umbrella structure of the anchoring mechanism passes through the atrial septum of the heart.

23. The method according to claim 1, wherein the sensing device and the readout device are part of a closed-loop pacing/ICD (cardioverter defibrillator) tuning system comprising a patient pacemaker and a pacing/ICD unit, wherein data from the sensing device is sent to the patient pacemaker for tailoring function of the pacing/ICD unit.

24. The method according to claim 23, wherein the sensing device is directly interrogated by the pacing/ICD unit.

25. The method according to claim 23, wherein the sensing device is interrogated by the pacing/ICD unit, and the method further comprises using an external unit for transmitting power to the sensing device.

26. The method according to claim 23, wherein the sensing device transmits data to the readout device, and the readout device retransmits the data to the pacing/ICD unit.

27. The method according to claim 26, wherein the readout device and the pacing/ICD unit perform at least one function of interrogation or powering of the sensing device.

28. A method of monitoring one or more physiological parameters useful in diagnosing and/or treating a cardiovascular disease within a patient, the method comprising:

providing a sensor comprising a hermetic sensor package containing at least one inductor coil and at least one sensing element operable to sense at least one physiological parameter of the patient, the sensor package having oppositely-disposed first and second portions;

assembling the sensor with an anchoring mechanism to form an implantable sensing device, the anchoring mechanism comprising oppositely-disposed first and second foldable umbrella structures located adjacent the first and second portions, respectively, of the sensor package, the first and second foldable umbrella structures having vertices that face away from each other, the sensor being assembled with the anchoring mechanism so that the sensor package thereof is between the first and second foldable umbrella structures, the second foldable umbrella structure being smaller than the first foldable umbrella structure;

implanting the sensing device by folding the first and second foldable umbrella structures of the anchoring mechanism, passing the first or second foldable umbrella structure through a septum of the heart of the patient to locate the second foldable umbrella structure within a cavity on the left side of the patient's heart, and expanding the first and second foldable umbrella structures to engage opposite sides of the septum, wherein the entire sensing device is within the heart, the sensor package is located in the septum and the at least one sensing element senses the at least one physiological parameter in the cavity, wherein the first foldable umbrella structure and the majority of the sensing device are located in the right side of the heart to minimize the risk of thrombogenicity;

operating the sensor to produce an output based on the at least one physiological parameter within the cavity of the patient;

coupling the sensor to a non-implantable readout device that is not implanted in the patient, the readout device comprising at least one inductor coil having telemetric means that receives the output of the sensor through the at least one inductor coil of the sensing device; and tailoring a medication treatment for treating the cardiovascular disease of the patient based on the output of the sensor.

* * * * *